US006262031B1

(12) United States Patent
Larouche et al.

(10) Patent No.: US 6,262,031 B1
(45) Date of Patent: Jul. 17, 2001

(54) METHOD FOR TREATING *PEDICULOSIS CAPITIS* INFESTATION

(75) Inventors: Stephanie Larouche, Princeton Junction, NJ (US); Cynthia Guzzo, Rydal, PA (US); Alfred J. Saah, Blue Bell, PA (US); Kenneth Brown, Philadelphia, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/523,335

(22) Filed: Mar. 10, 2000

Related U.S. Application Data

(60) Provisional application No. 60/124,309, filed on Mar. 12, 1999.

(51) Int. Cl.$^7$ .................................................. A61K 31/70
(52) U.S. Cl. ................................................ 514/30; 514/27
(58) Field of Search ........................................ 514/27, 30

(56) References Cited

PUBLICATIONS

Glaziou, P., et al., "Efficacy of ivermectin for the treatment of head lice (*Pediculosis capitis*),", *Rop. Med. Parasitol.* 45, pp. 253–254, (1994).
Youssef, Magda, Y.M., et al., "Topical Application of Ivermectin for Human Ectoparasites", *Am. J. Trop. Med. Hyg.*, 53 (6), pp. 652–653, (1995).
Mumcuoglu, K.Y., et al., "Systemic Activity of Ivermectin on the Human Body Louse (Anoplura: Pediculidae)," *J. Med. Entomol.* 27 (1), pp. 72–75 (1990).
Schachner, Lawrence A., "Treatment Resistant Head Lice: Alternative Therapeutic Approaches," *Pediatric Dermatology*, vol. 14 No. 5 409–410, (1997).
Bell, Thomas A., "Treatment of Pediculus Humanus Var. Capitis Infestation in Cowlitz County, Washington, with Ivermectin and the Licemeister Comb," *The Pediatric Infectous Disease Journal*, vol. 17, No. 10, Oct., (1998).
Burkhart, Craig G., "An assessment of topical and oral prescription and over–the–counter treatments for head lice," *Journal of the American Academy of Dermatology*, pp. 979–982, Jun. (1998).
"Drugs for Head Lice," *The Medical Letter*, vol. 39 (issue 992), pp. 6–8, Jan. 17, 1997.

Lertzman, Beth H., et al., "Drug Treatment of Skin and Soft Tissue Infections in Elderly Long–Term Care Residents," *Drugs & Aging*, 9 (2), 1996.
Liu, Leo X., et al., "Antiparastic Drugs," *The New England Journal of Medicine*, pp. 1178–1184, May 2, (1996).
Ottesen, Eric A. et al., "Review: Ivermectin in human medicine," *Journal of Antimicrobial Chemotherapy*, 34, 195–203 (1994).
Mumcuoglu, K. Y., et al., "Scientific Meetings of Israel," *Israel Journal of Medical Sciences*, vol. 26, No. 11, p. 658, Nov. (1990).
Dunne, C.L., et al., "A field study of the effects of ivermectin on ectoparasites of man," *Transactions of the Royal Society of Tropical Medicine and Hygiene*, 85, pp. 550–551 (1991).
Eichenfield, Lawrence F., et al., "Treatment of Head Lice," *Concise Reviews of Pediatric Infectious Diseases*, pp. 420–422, May (1998).
*PDR* entry for Stromectol, Oct. 1998.
"Mectizan (Ivermectin, MSD)," *International Physicians Circular*, Merck Sharp & Dohme, pp. 1–4, Jul. 1990.

Primary Examiner—Elli Peselev
(74) *Attorney, Agent, or Firm*—Richard S. Parr; Melvin Winokur

(57) ABSTRACT

A method for treating *Pediculosis capitis* infestation in a human patient which comprises orally administering to the human a total amount of ivermectin of between about 400 ug/kg and about 1200 ug/kg over a period of time of about one week, wherein equal portions of the total amount are administered according to an administration sequence selected from the group consisting of c) a first day and a second day, and d) a first day, a second day and a third day, during the one week time period.

The invention is also a method for treating *Pediculosis capitis* infestation in a human patient which comprises orally administering to the human a total amount of ivermectin of between about 6 mg and 135 mg over a period of time of about one week, wherein equal portions of the total amount are administered according to an administration sequence selected from the group consisting of e) a first day and a second day, and f) a first day, a second day and a third day, during the one week time period.

17 Claims, No Drawings

METHOD FOR TREATING *PEDICULOSIS CAPITIS* INFESTATION

CROSS-REFERENCE TO RELATED APPLICATION

This application claims the benefit of provisional application No. 60/124,309, filed Mar. 12, 1999.

BACKGROUND OF THE INVENTION

Ivermectin is a semisynthetic, anthelmintic agent derived from the avermectins, a class of highly active broad-spectrum anti-parasitic agents isolated from the fermentation products of Streptomyces avermitilis. Ivermectin is a mixture containing at least 90% 5-O-demethyl-22,23-dihydroavermectin $A_{1a}$ and less than 10% 5-O-demethyl-25-de(1-methylpropyl)-22,23-dihyro-25-(1-methylethyl) avermectin $A_{1a}$, generally referred to as 22,23-dihydroavermectin $B_{1a}$ and $B_{1b}$, or $H_2B_{1a}$ and $H_2B_{1b}$, respectively. Ivermectin is described in U.S. Pat. No. 4,199,569. The structural formulas are:

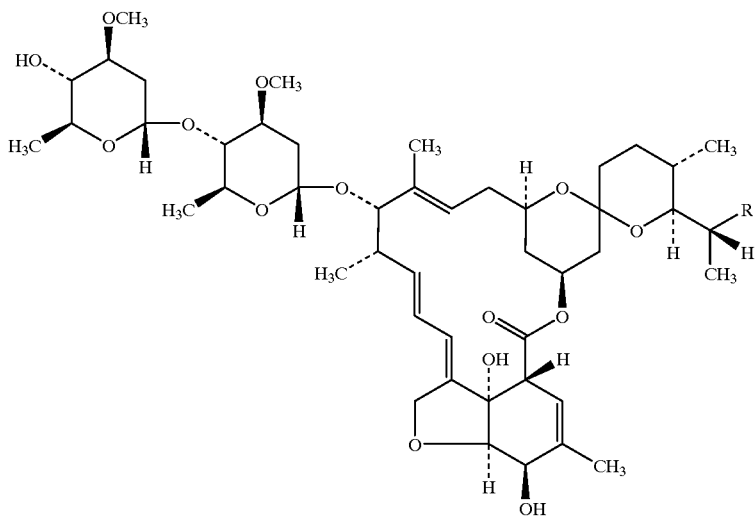

The compound selectively binds with high affinity to glutamate-gated chloride ion channels which occur in invertebrate nerve and muscle cells, leading to an increase in the permeability of the cell membrane to chloride ions with hyperpolarization of the nerve or muscle cell, resulting in paralysis and death of the parasite. The selectivity of the compound is attributable to the facts that some mammals do not have glutamate gated chloride channels and that the compound has a low affinity for mammalian ligand-gated chloride channels. Ivermectin does not readily cross the blood brain barrier in humans.

Ivermectin is active against various life-cycle stages of many but not all nematodes. It is active against the tissue microfilariae of *Onchocerca volvulus* but not against the adult form. Its activity against *Strongyloides stercoralis* is limited to the intestinal stages.

Ivermectin is commercially available as STROMECTOL® for eradication of *Strongyloides stercoralis*, which causes strongyloidiasis, and *Onchocerca volvulus*, which causes onchocerciasis. Ivermectin is also available as MECTIZAN® for eradication of *Onchocerca volvulus*. Ivermectin has a plasma half-life of about 12 hours. Its metabolite has a plasma half life of about 3 days.

The recommended dosage for treating strongyloidiasis is a single oral dose designed to provide approximately 240–170 ug of ivermectin per kg of body weight (e.g. one 6 mg tablet administered to a 25–35 kg patient). Additional doses are not necessary in order to eradicate infection.

The recommended dosage for treating onchocerciasis is a single oral dose designed to provide approximately 230–140 ug of ivermectin per kg of body weight (e.g. one 6 mg tablet administered to a 26–44 kg patient). The most commonly used dose intervals in mass distribution campaigns is 12 months. However, retreatment of individuals may be considered at intervals as short as 3 months. Clinical trials have demonstrated efficacy and tolerability that effectively reduces the dermal microfilarial density to near zero after one month and to successfully maintain a low microfilarial level for up to 12 months.

Ivermectin is also used to treat microfilaremia in patients with lymphatic filariasis caused by Wuchereria bancrofti. Ivermectin has not been shown to have any activity against adult worm of any species of Filarioidea causing lymphatic filariasis, in tropical pulmonary eosinophilia syndrome, or in lymphadenitis or lymphangitis associated with lymphatic filariasis. Ivermectin is recommended for use in treating microfilaremia in lymphatic filariasis in patients for whom there may be an increased risk of adverse experiences with the use of other microfilaricides, such as in populations of patients who are, or are likely to be co-infected with *Onchocerca volvulus*. The recommended dosage for mass distribution for the treatment of microfilaremic in lymphatia filariasis is a single oral dose of approximately 150 to 200 ug/kg once every 6 months. In endemic areas where treatment can only be administered once every 12 months, a dose of approximately 300 to 400 ug/kg is recommended. These doses are based on studies conducted in patients in Africa, Asia, South America and the Caribbean. Ivermectin was compared with diethylcarbamazine in some of these studies. Overall incidences of adverse experiences for an amicrofilaremic population in mass treatment programs were 1%. The following is a list of the more common adverse experiences reported in studies of microfilaremic patients in the literature: fever, headache, myalgia, asthenia/weakness, cough, anorexia, chills, lethargy, arthralgia, nausea, diaphoresis, sore throat, abdominal pain, light-headedness, malaise epigastric pain, postural hypotension, lung function alterations, dizziness, body pain, gastralgia, chest pain, fatigue, respiratory adverse experiences, testicular tenderness, and ascaris expulsion/elimination of worms. The frequency and intensity of adverse experiences are probably related to the pretreatment microfilarial density. Laboratory abnormalities included eosinophilia, liver function abnormalities and hematuria.

Ivermectin has been used to treat head lice (*Pediculosis capitis*). Glaziou et al. Trop. Med. Parasitol. 45 (1994) 253–254 describe a study in which 26 patients each received a single oral 200 ug/kg dose. The results showed an effectiveness of ivermectin 200 mcg/kg single dose against head lice. The authors suggested a second dose on the tenth day to prevent reinfestation from others in the population with head lice. The second dose was not suggested as part of the treatment regimen for the initial infestation.

Magda et al. Amer. J. Trop. Med. Hyg. 53(6) 1995 pp. 652–653 describe a method of topical application of ivermectin to treat head lice. Ivermectin was found to have an absolute curative effect after a single topical application.

Dunne et al. Trans. R. Soc. Trop. Med. Hyg. 85: 550–551 describe a study in which a single oral dose of 100–200 ug/kg of ivermectin was administered to patients with head lice. They reported a significant, but not absolute, effect on head lice infestation.

The present invention is a method for treating head lice infestation by orally administering to the patient, over a period of time of about one week, a total amount of ivermectin of between about 400 ug/kg and 1200 ug/kg.

SUMMARY OF THE INVENTION

The invention is a method for treating *Pediculosis capitis* infestation in a human which comprises orally administering to the human an amount of ivermectin of between about 400 ug/kg and about 1200 ug/kg (e.g. 400 ug/kg, 600 ug/kg, 800 ug/kg and 1200 ug/kg) over a period of time of about one week wherein equal portions of the total amount are administered according to an administration sequence selected from the group consisting of a) a first day and a second day, and b) a first day, a second day, and a third day. The amount is administered in equal portions on two separate days or three separate days during the one week time period (e.g. a 200 ug/kg delivered on Day 1 and 200 ug/kg delivered on Day 8 would deliver a total of 400 ug/kg).

DETAILED DESCRIPTION OF THE INVENTION

The invention is a method for treating *Pediculosis capitis* infestation in a human which comprises orally administering to the human an amount of ivermectin of between about 400 ug/kg and about 1200 ug/kg (e.g. 400 ug/kg, 600 ug/kg, 800 ug/kg and 1200 ug/kg) over a period of time of about one week wherein equal portions of the total amount are administered according to an administration sequence selected from the group consisting of a) a first day and a second day, and b) a first day, a second day, and a third day. The amount is administered in equal portions on two separate days or three separate days during the one week time period (e.g. a 200 ug/kg delivered on Day 1 and 200 ug/kg delivered on Day 8 would deliver a total of 400 ug/kg).

In the instance where administration is on two separate days in two equal portions, the first portion is administered on a first day (Day 1) and the second portion is administered on a second day about one week later (e.g. on Day 7, Day 8, or Day 9).

The term "about one week" means seven, eight or nine days. Day 7 is the sixth day following Day 1 (i.e., Day 1 and Day 7 are six days apart). The period of time when administration occurs on Day 1 and Day 7 is seven days. Day 8 is the seventh day following Day 1 (i.e., Day 1 and Day 8 are seven days apart). The period of time when administration occurs on Day 1 and Day 8 is eight days. Day 9 is the eighth day following Day 1 (i.e., Day 1 and Day 9 are eight days apart). The period of time when administration occurs on Day 1 and Day 9 is nine days.

The abbreviation "ug" used throughout the application, represents "micrograms." The abbreviation "ug/kg", used to represent doses of ivermectin administered to patients treated in accordance with the procedure of the invention, represents the number of micrograms per kilogram weight of the patient. For example, a 100 kg patient, receiving a dose of ivermectin of 200 ug/kg, would be receiving 20 mg.

The method of the invention involves multiple dosing of ivermectin in order to eradicate head lice infestation. According to the method, the first dose is administered after identification of infestation, evidenced by the presence of lice or eggs (nits) on the patient. The first dose kills lice present at the time of dosing. Subsequent dosing, e.g., on Day 8 only, or on Days 4 and 8, kills lice that is unhatched when the first dose is administered, in addition to lice that may have survived initial dosing. Doses are administered to the patient by providing the patient with oral tablets (e.g. 3 mg tablets) in quantities sufficient to achieve the specified dose amount of ivermectin. The number of tablets to be administered depends on the weight of the patient.

In one embodiment of the invention, the patient receives a total amount of ivermectin of between about 400 ug/kg and 600 ug/kg. For example, the patient receives about 200 ug/kg on Day 1 and about 200 ug/kg on Day 8. In another example, the patient receives about 200 ug/kg on Day 1, about 200 ug/kg on Day 4 and about 200 ug/kg on Day 8.

In another embodiment of the invention, the patient receives a total amount of ivermectin of between about 800 ug/kg and 1200 ug/kg. For example, the patient receives about 400 ug/kg on Day 1 and about 400 ug/kg on Day 8. In another example, the patient receives about 400 ug/kg on Day 1, about 400 ug/kg on Day 4 and about 400 ug/kg on Day 8.

In another embodiment of the invention, the patient receives on treatment days 1 and 8 a total amount of ivermectin of between 400 ug/kg (200 ug/kg on Day 1 and 200 ug/kg on Day 8) and 800 ug/kg (400 ug/kg on Day 1 and 400 ug/kg on Day 8) along with food during dosing on Day 1 and during dosing on Day 8. In another embodiment of the invention, the patient receives on treatment days 1 and 8 a total amount of ivermectin of between 400 ug/kg (200 ug/kg on Day 1 and 200 ug/kg on Day 8) and 800 ug/kg (400 ug/kg on Day 1 and 400 ug/kg on Day 8) without food.

In another embodiment of the invention, the patient receives on treatment days 1 and 8 a total amount of ivermectin of between 400 ug/kg (200 ug/kg on Day 1 and 200 ug/kg on Day 8) and 800 ug/kg (400 ug/kg on Day 1 and 400 ug/kg on Day 8) followed by shampoo cleanings after dosing on Day 1 and dosing on Day 8. In another embodiment of the invention, the patient receives on treatment days 1 and 8 a total amount of ivermectin of between 400 ug/kg (200 ug/kg on Day 1 and 200 ug/kg on Day 8) and 800 ug/kg (400 ug/kg on Day 1 and 400 ug/kg on Day 8) without shampooing.

In another embodiment of the invention, the patient receives on treatment days 1 and 8 a total amount of ivermectin of between 400 ug/kg (200 ug/kg on Day 1 and 200 ug/kg on Day 8) and 800 ug/kg (400 ug/kg on Day 1 and 400 ug/kg on Day 8) along with food during dosing on Day 1 and during dosing on Day 8, and followed by shampoo cleanings after dosing on Day 1 and dosing on Day 8.

The term "about", with regard to doses of ivermectin, includes amounts of ivermectin above or below the target dose which are delivered to the patient by a number of undivided 3 mg or 6 mg tablets given to a patient of specified weight. Tables 1 and 2 indicate the dose achieved by giving a patient within a given weight range a specified number of 3 mg tablets. Table 1 shows, for example, that a 90 kg patient taking 5 tablets would receive a dose of 167 ug/kg. This amount is encompassed by the phrase "about 200 ug/kg". Tables 3 and 4 indicate the dose achieved by giving a patient within a given weight range a specified number of 6 mg tablets. Table 4 shows, for example, that a 79 kg patient taking 5 tablets would receive a dose of 380 ug/kg. This amount is encompassed by the phrase "about 400 ug/kg".

The following tables show the number of 3 mg tablets which are administered to a patient, having a weight within the indicated weight range, in order to deliver the target dose of about 200 ug/kg or about 400 ug/kg.

TABLE 1

200 ug/kg dosing guidelines

| Weight range (kg) | #3 mg tablets | Actual dose delivered |
|---|---|---|
| 15–21 | 1 | 143–200 ug/kg |
| 22–40 | 2 | 150–273 ug/kg |
| 41–60 | 3 | 150–220 ug/kg |
| 61–75 | 4 | 160–197 ug/kg |
| 76–90 | 5 | 167–197 ug/kg |
| 91–105 | 6 | 171–198 ug/kg |
| 106–140 | 7 | 150–198 ug/kg |

TABLE 2

400 ug/kg dosing guidelines

| Weight range (kg) | #3 mg tablets | Actual dose delivered |
|---|---|---|
| 15–19 | 2 | 316–400 ug/kg |
| 20–26 | 3 | 346–450 ug/kg |
| 27–33 | 4 | 364–444 ug/kg |
| 34–39 | 5 | 385–441 ug/kg |
| 40–52 | 6 | 346–450 ug/kg |
| 53–66 | 8 | 364–453 ug/kg |
| 67–79 | 10 | 380–448 ug/kg |
| 80–99 | 12 | 364–450 ug/kg |
| 100–140 | 15 | 321–450 ug/kg |

The following tables show the number of 6 mg tablets which are administered to a patient, having a weight within the indicated weight range, in order to deliver the target dose of about 200 ug/kg or about 400 ug/kg.

TABLE 3

200 ug/kg dosing guidelines

| Weight range (kg) | #6 mg tablets | Actual dose delivered |
|---|---|---|
| 27–48 | 1 | 125–222 ug/kg |
| 49–66 | 2 | 181–245 ug/kg |
| 67–105 | 3 | 171–269 ug/kg |
| 106–140 | 4 | 171–226 ug/kg |

TABLE 4

400 ug/kg dosing guidelines

| Weight range (kg) | #6 mg tablets | Actual dose delivered |
|---|---|---|
| 27–36 | 2 | 364–444 ug/kg |
| 37–52 | 3 | 333–487 ug/kg |
| 53–66 | 4 | 364–453 ug/kg |
| 67–79 | 5 | 380–448 ug/kg |
| 80–99 | 6 | 364–450 ug/kg |
| 100–140 | 7 | 300–420 ug/kg |

The invention also includes a method for treating *Pediculosis capitis* infestation in a human patient which comprises orally administering to the human a total amount of ivermectin of between about 6 mg and 135 mg over a period of time of about one week, wherein equal portions of the total amount are administered according to an administration sequence selected from the group consisting of a) a first day and a second day, and b) a first day, a second day and a third day, during the one week time period.

In one class of the invention, the total amount of ivermectin is selected from the group of amounts consisting of 6 mg, 9 mg, 12 mg, 18 mg, 24 mg, 27 mg, 30 mg, 36 mg, 42 mg, 45 mg, 48 mg, 54 mg, 60 mg, 63 mg, 72 mg, 84 mg, 90 mg, 108 mg, 126 mg, and 135 mg. The administration sequence may include administration, in equal amounts, on a first day and a second day, e.g. wherein the first day and the second day are about one week apart, e.g. about seven days apart.

In a subclass of this class, the method comprises administering to the human an amount of ivermectin selected from the group consisting of a) 3 mg on the first day and 3 mg on the second day, b) 6 mg on the first day and 6 mg on the second day, c) 9 mg on the first day and 9 mg on the second day, d) 12 mg on the first day and 12 mg on the second day, e) 15 mg on the first day and 15 mg on the second day, f) 18 mg on the first day and 18 mg on the second day, g) 21 mg on the first day and 21 mg on the second day, and h) 24 mg on the first day and 24 mg on the second day.

In another subclass of this class, the method comprises administering to the human an amount of ivermectin selected from the group consisting of a) 6 mg on the first day and 6 mg on the second day, b) 9 mg on the first day and 9 mg on the second day, c) 12 mg on the first day and 12 mg on the second day, d) 15 mg on the first day and 15 mg on the second day, e) 18 mg on the first day and 18 mg on the second day, f) 24 mg on the first day and 24 mg on the second day, g) 30 mg on the first day and 30 mg on the second day, h) 36 mg on the first day and 36 mg on the second day i) 42 mg on the first day and 42 mg on the second day, and j) 45 mg on the first day and 45 mg on the second day.

In a group of either subclasses of the invention, the method involves administration to a patient in a non-fasting state.

Doses of ivermectin administered in accordance with the invention may be administered to a fasting human patient or a non-fasting human patient (a patient consuming food about the time of ivermectin administration). A non-fasting human patient is one who consumes food or beverage in quantities sufficient to deliver food or beverage to the stomach which eliminates physical conditions associated with a fasting state. Meals, such as breakfast, lunch, and dinner, composed of carbohydrates, fat and protein representative of a breakfast, lunch or dinner typical of a normal balanced diet, and food or beverage snacks such as cookies, cheese or milk, are exemplary of such foods and beverages. Such food or beverage, ingested within one hour before drug administration, or within two hours after drug administration, induces the non-fasting state. Thus, a patient ingesting food or beverage one hour before administration of the drug, two hours after drug administration, or any time during that three hour interval, is administering the drug in a non-fasting state.

Doses of ivermectin administered in accordance with the invention may be followed by shampoo hair cleanings with shampoos typically used for cleaning hair such as PRELL® shampoo (e.g., those which clean hair but which do not contain active ingredients known to be useful for killing head lice, such as permethrin, lindane, pyrethrin, carbaryl, and malathion).

It is also contemplated that the method of the present invention is useful for preventing head lice infestation in a human susceptible to such infestation, e.g. a human coming into close contact with an infected individual.

The method of the present invention is also useful in oral or topical combination with other known head lice treatments, including, but not limited to, treatments with permethrin (NIX®, ELIMITE®, lindane (KWELL®, SCABENE®), pyrethrin (including A200 shampoo, Clear Total Lice Elimination System, and Maximum Strength Rid Lice Killing Shampoo), carbaryl, malathion, formic acid rinses, combing, including thermal combing, and shampooing, including shampooing with enzymes that dissolve chitinous cement on nits. It is also contemplated that oral forms of moxidectin, the active ingredient in QUEST™ Gel, as well as oral forms of doramectin, would be suitable for treating head lice infestation by oral dosing in accordance with treatment regimens described herein. It is also contemplated that oral administration of ivermectin, in accordance with the treatment regimen of the present invention, can be supplemented with topical administration, using the method of topical administration, for example, described in Magda et al. Amer. J. Trop. Med. Hyg. 53(6) 1995 pp. 652–653. It is also contemplated that abamectin (U.S. Pat. No. 4,310,519) (5-O-demethylavermectin $A_{1a}$ and 5-O-demethyl-25-de(1-methylpropyl)-25-(1-methylethyl) avermectin $A_{1a}$ (4:1)) may be used to treat head lice infestation in accordance with the procedures described in the subject application.

EXAMPLE 1
Tablet Preparation

Tablets containing 3 mg, of ivermectin are prepared as illustrated below (compositions A, B, and C)

| Component | Amount - mg | | |
|---|---|---|---|
|  | A | B | C |
| Ivermectin | 3 | 3 | 3 |
| Microcrystalline cellulose | 37.25 | 100 | 200 |
| Modified food corn starch | 37.2 | 5 | 4.25 |
| Magnesium stearate | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 3 mg, respectively, of active ingredient per tablet.

EXAMPLE 2

Comparison of head lice treatment using orally administered ivermectin at cumulative doses of 200 ug/kg, 400 ug/kg and 600 ug/kg Patients infested with head lice were treated with one or more oral doses of ivermectin over a period of 8 days, and evaluated during that time and up to 15 days following initiation of treatment. On Days 1, 4, 8 and 15, patients had their scalp inspected for viable nits and their hair shampooed (prior to dosing, if the day for scalp inspection was also a "dosing" day). The rinse water was filtered through a towel that enabled the number of lice (for each stage of nymphs and/or adult lice) to be recorded. An independent qualitative assessment was performed on a subset of towels. All patients were also seen on Days 5 and 9 for the assessment of clinical adverse experiences.

The primary analysis was based on treatment outcome (success or failure) on Day 15. "treatment success" is defined to mean that no live lice were observed on Day 15. "Reinfestation" corresponds to the condition where the patient, previously free of lice (including any stage nymphs and/or adult lice) on Day 8, is infested thereafter with adult lice. "Reinfestation" also corresponds to the condition where the patient, previously free of lice and nits, is infested thereafter with adult lice and first and second stage nymphs. The percent of treatment success was calculated.

Three groups of patients were treated. Group 1 was treated with an oral dose of 200 ug/kg of ivermectin on Day 1 and subsequently evaluated for the presence of nymphs and/or adult lice on Day 15. Group 2 was treated with a first oral dose of 200 ug/kg of ivermectin on Day 1 and a second oral dose of 200 ug/kg of ivermectin on Day 8. Group 3 was treated with a first oral dose of 200 ug/kg of ivermectin on Day 1, a second oral dose of 200 ug/kg of ivermectin on Day 4, and a third oral dose of 200 ug/kg of ivermectin on Day 8.

| Treatment Group | Number of patients | Treatment success (%) Day 15 |
|---|---|---|
| 1 | 29 | 52% |
| 2 | 28 | 68% |
| 3 | 31 | 81% |

The results show that the highest success rate was achieved by treating patients with 200 ug/kg doses administered in Days 1, 4, and 8.

EXAMPLE 3

The procedure described in Example 2 was repeated with the exception that the doses administered were increased from 200 ug/kg to 400 ug/kg.

EXAMPLE 4

The procedure of Example 2 was repeated with the additional step of shampooing with an enzyme that dissolves chitinous cement on nits 8 hours after administration of each dose of ivermectin.

EXAMPLE 5

The procedure of Example 3 was repeated with the additional step of shampooing with an enzyme that dissolves chitinous cement on nits 8 hours after administration of each dose of ivermectin.

EXAMPLE 6

The procedure of Example 2 was repeated with the additional step of administering permethrin according to procedures for administering permethrin which are described in the Physician's Desk Reference, 52$^{nd}$ Edition (1998), page 9280.

EXAMPLE 7

Patients were administered 30 mg ivermectin while fasting. Three weeks later, the same patients were administered 30 mg ivermectin with a high fat meal. Comparison of patient ivermectin plasma levels in fasted and fed state indicated bioavailability of ivermectin was increased 2.5 times.

EXAMPLE 8

Comparison of head lice treatment using orally administered ivermectin at cumulative doses of 800 ug/kg, 1200 ug/kg and 600 ug/kg and shampoo cleaning Patients infested with head lice were treated with oral doses of ivermectin over a period of 8 days, and evaluated during that time and up to 15 days following initiation of treatment. On Days 1, 4 and 8, patients had their scalp inspected for nits and lice. Their hair was shampooed on Days 2, 5, 9, and 15. The rinse water was filtered through a towel that enabled the number of lice (for each stage of nymph and/or adult lice) to be recorded. An independent qualitative assessment was performed on those towels with live lice at Day 15. Clinical adverse experiences were collected at all visits.

The primary analysis was based on treatment outcome (success or failure) on Day 15. "Treatment success" is defined to mean that no live lice were observed on Day 15, or, if lice were present on Day 15, that they were the result of reinfestation. "Reinfestation" corresponds to the condition where the patient, previously free of lice (including any stage nymphs and/or adult lice) on Day 9, is infested thereafter with adult lice. Patients who were reinfested were counted as successes. The percent of treatment success was calculated.

Three groups of patients were treated. Group 1 was treated with an oral dose of 400 ug/kg of ivermectin on Day 1 and an oral dose of 400 ug/kg of ivermectin on Day 8 and subsequently evaluated for the presence of nymphs and/or adult lice on Day 15. Group 2 was treated with a first oral dose of 400 ug/kg of ivermectin on Day 1, a second oral dose of 400 ug/kg of ivermectin on Day 4, and a third oral dose of 400 ug/kg of ivermectin on Day 8. Group 3 was treated with a first oral dose of 200 ug/kg of ivermectin on Day 1, a second oral dose of 200 ug/kg of ivermectin on Day 4, and a third oral dose of 200 ug/kg of ivermectin on Day 8. All patient groups in this example received washing shampoos (which contained no lice killing active ingredients) the day following each administration of ivermectin.

| Treatment Group | Number of patients | Treatment success (%) Day 15 |
|---|---|---|
| 1 | 57 | 98.2% |
| 2 | 60 | 100% |
| 3 | 57 | 100% |

The results show that all three study groups received comparable success rates on Day 15.

What is claimed is:

1. A method for treating *Pediculosis capitis* infestation in a human patient which comprises orally administering to the human a total amount of ivermectin of between about 800 ug/kg and about 1200 ug/kg over a period of time of about one week, wherein equal portions of the total amount are administered according to an administration sequence selected from the group consisting of a) a first day and a second day, and b) a first day, a second day and a third day, during the one week time period.

2. A method of claim 1, wherein the administration sequence is a first day and a second day.

3. A method of claim 2, wherein the first day and the second day are about one week apart.

4. A method of claim 3, wherein the first day and the second day are seven days apart.

5. A method of claim 4, wherein ivermectin is administered with food.

6. A method of claim 4 for treating *Pediculosis capitis* infestation in a human which comprises administering to the human an amount of ivermectin of about 400 ug/kg on the first day and about 400 ug/kg on the second day.

7. A method of claim 1 for treating *Pediculosis capitis* infestation in a human wherein the administration sequence is a first day, a second day, and a third day, which comprises administering to the human an amount of ivermectin of about 400 ug/kg on the first day, about 400 ug/kg on the second day and about 400 ug/kg on the third day.

8. A method for treating *Pediculosis capitis* infestation in a human patient which comprises orally administering to the human a total amount of ivermectin of between about 12 mg and 135 mg over a period of time of about one week, wherein equal portions of the total amount are administered according to an administration sequence selected from the group consisting of a) a first day and a second day, and b) a first day, a second day and a third day, during the one week time period.

9. A method of claim 8 wherein the total amount of ivermectin is selected from the group of amounts consisting of 12 mg, 18 mg, 24 mg, 27 mg, 30 mg, 36 mg, 42 mg, 45 mg, 48 mg, 54 mg, 60 mg, 63 mg, 72 mg, 84 mg, 90 mg, 108 mg, 126 mg, and 135 mg.

10. A method of claim 9, wherein the administration sequence is a first day and a second day.

11. A method of claim 10, wherein the first day and the second day are about one week apart.

12. A method of claim 11, wherein the first day and the second day are seven days apart.

13. A method of claim 12 which comprises administering to the human an amount of ivermectin selected from the group consisting of b) 6 mg on the first day and 6 mg on the second day, c) 9 mg on the first day and 9 mg on the second day,
d) 12 mg on the first day and 12 mg on the second day,
e) 15 mg on the first day and 15 mg on the second day,
f) 18 mg on the first day and 18 mg on the second day,
g) 21 mg on the first day and 21 mg on the second day, and
h) 24 mg on the first day and 24 mg on the second day.

14. A method of claim 12 which comprises administering to the human an amount of ivermectin selected from the group consisting of
a) 6 mg on the first day and 6 mg on the second day,
b) 9 mg on the first day and 9 mg on the second day,
c) 12 mg on the first day and 12 mg on the second day,
d) 15 mg on the first day and 15 mg on the second day,
e) 18 mg on the first day and 18 mg on the second day,
f) 24 mg on the first day and 24 mg on the second day,
g) 30 mg on the first day and 30 mg on the second day,
h) 36 mg on the first day and 36 mg on the second day
i) 42 mg on the first day and 42 mg on the second day, and
j) 45 mg on the first day and 45 mg on the second day.

15. A method of claim 13, wherein ivermectin is administered with food.

16. A method of claim 14, wherein ivermectin is administered with food.

17. A method for treating *Pediculosis capitis* infestation in a human patient which comprises orally administering to the human a total amount of ivermectin of about 800 ug/kg over a period of time of about one week, wherein equal portions of the total amount are administered according to an administration sequence having a first day and a second day.

* * * * *